United States Patent
Daikuzono et al.

[11] Patent Number: 5,851,112
[45] Date of Patent: Dec. 22, 1998

[54] DENTAL HANDPIECE

[75] Inventors: Norio Daikuzono, Cincinnati, Ohio; Hidetoshi Motoori, Tokyo, Japan

[73] Assignee: S.L.T. Japan Co., Ltd., Tokyo, Japan

[21] Appl. No.: 903,792

[22] Filed: Jul. 31, 1997

[51] Int. Cl.$^6$ ........................................ A61C 1/00
[52] U.S. Cl. ................................. 433/29; 606/16
[58] Field of Search ........................ 433/29; 606/13, 606/14, 15, 16

[56] References Cited

U.S. PATENT DOCUMENTS

| | | | |
|---|---|---|---|
| 4,608,980 | 9/1986 | Aihara | 606/16 |
| 4,826,431 | 5/1989 | Fujimura et al. | 433/29 |
| 5,221,279 | 6/1993 | Cook et al. | 606/15 |
| 5,346,489 | 9/1994 | Levy et al. | 606/15 |
| 5,409,376 | 4/1995 | Murphy | 433/29 |

FOREIGN PATENT DOCUMENTS

| | | |
|---|---|---|
| 0523506 A1 | 1/1993 | European Pat. Off. |
| 5-501075 | 3/1993 | Japan . |
| 5-28142 | 4/1993 | Japan . |
| 5-245165 | 9/1993 | Japan . |
| 5-86227 | 12/1993 | Japan . |
| 94/10923 | 5/1994 | WIPO . |

*Primary Examiner*—John J. Wilson
*Attorney, Agent, or Firm*—McDermott, Will & Emery

[57] ABSTRACT

A dental handpiece 1 having a laser irradiation switch 5 on a hand grip 2 portion and a bent guide tube 6A through which an optical fiber 7 for introducing laser light to its distal end is inserted, is characterized in that said laser irradiation switch 5 can be rotated around the longitudinal axis of the handpiece 1 together with a holder member 3 which is fitted on the outer periphery of the hand grip 2 and a part (2A) of the hand grip holder 2.

3 Claims, 10 Drawing Sheets

DENTAL HANDPIECE

BACKGROUND OF THE INVENTION a) Field of the Invention

The present invention relates to a dental handpiece and in particular to a dental handpiece which is used for intraoral treatment such as incision, hemostasis and resolution, preventive treatment of dental caries, prevention of progressive initial dental caries, and the removal of dental calculus and bacterial plaque by irradiating the dental bud with laser light.

b) Description of the Related Art

Recently, attempts at dental treatment have been made by irradiating the tooth bud with laser light for dental caries treatment, intra oral treatment such as incision, hemostasis and resolution, enhancement of tooth quality by providing the surface of tooth bud tissue with acid resistance, the prevention of progression of initial dental caries, and removal of dental calculus and dental plaque. The dental laser devices are disclosed in, for example, Japanese Examined Patent Publication No. Hei 5-86227, Japanese Unexamined PCT Publication No. Hei 5-501075 and Japanese Examined Patent Publication No. Hei 5-28142.

Dental handpieces which are provided with a switch for turning on or off of the laser to prevent erroneous actuation of the switch and/or incorrect irradiation of an adjacent healthy tooth bud tissue are disclosed in Japanese Examined Patent Publication Nos. Hei 5-245165 and Hei 1-91848.

When the intraoral treatment or the tooth bud treatment is conducted by means of a handpiece with the above-mentioned switch, the handpiece is actuated while a finger is constantly placed on the switch in order to quickly conduct turning on or off of the laser light irradiation. A surgical operator conducts treatment in such a manner that a portion to be treated is constantly irradiated with laser light by bending his arm, twisting his wrist or bending himself backward while maintaining a fixed relative relationship between the holding hand and the handpiece. There is a problem that the operator feels pain on his body or fatigue since the forced posture or condition should be maintained during treatment of, particularly the upper jaw, the side of the oral cavity and the side of the tooth bud.

SUMMARY OF THE INVENTION

It is therefore an object of the present invention to provide a dental handpiece which enables an operator to easily actuate a switch while irradiating a portion to be treated with laser light without the necessity of bending his arm or twisting his wrist during treatment of the upper jaw, the side of the oral cavity, or the side of the tooth bud.

In order to achieve the above-mentioned object, in a first aspect of the present invention, there is provided a dental handpiece having a laser irradiation switch on a hand grip portion and a bent guide tube through which an optical fiber for introducing laser light to its distal end is inserted, characterized in that said laser irradiation switch can be rotated around the longitudinal axis of the handpiece together with a holder member which is fitted on the outer periphery of the hand grip and a part of the hand grip holder.

Accordingly, treatment can be conducted while positioning the irradiation enabling switch depending upon the portion to be treated in such a position where the switch is most readily actuated, since the position of the laser irradiation enabling switch can be angularly changed to a desired position in accordance with the present invention. Therefore, the operator can always perform the surgical operation in a comfortable posture without bending his arm, twisting his wrist, or bending himself backward as is done in the prior art.

In a second aspect of the present invention, there is provided a dental handpiece having a laser irradiation switch on a hand grip portion and a bent guide tube through which an optical fiber for introducing laser light to its distal end is inserted, characterized in that said bent guide tube can be rotated around the longitudinal axis of the hand grip.

DESCRIPTION OF THE DRAWINGS

The present invention will be described by way of embodiments with reference to drawings, in which.

DESCRIPTION OF THE PREFERRED EMBODIMENTS

Referring now to FIGS. 1 to 4, shown therein are elevational and longitudinal sectional views showing a first dental handpiece 1 the according to the present invention (hereinafter referred to as "handpiece").

Figure 1:
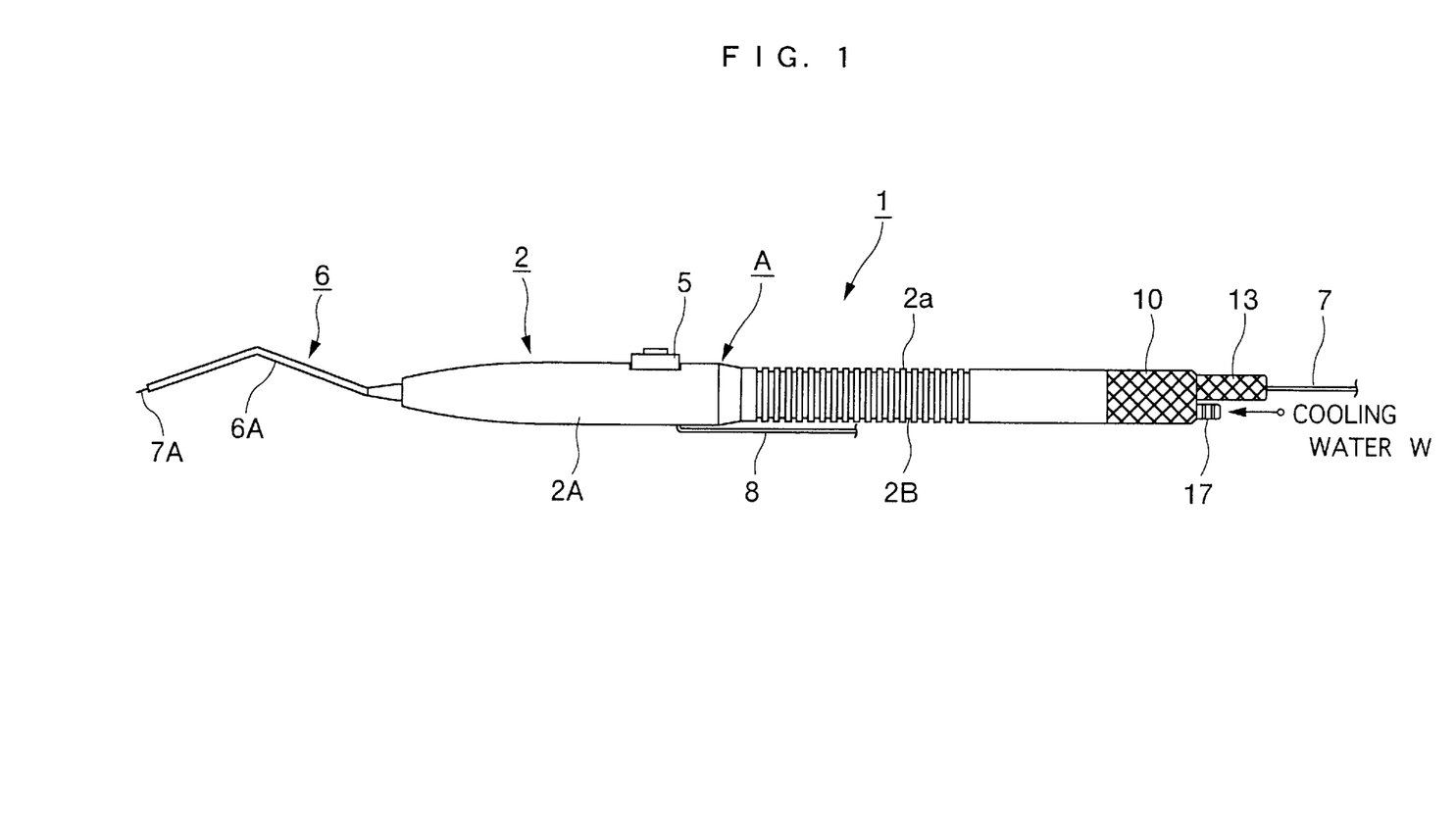
FIG. 1 is a view showing a handpiece 1 of a first embodiment of the present invention.
Figure 2:
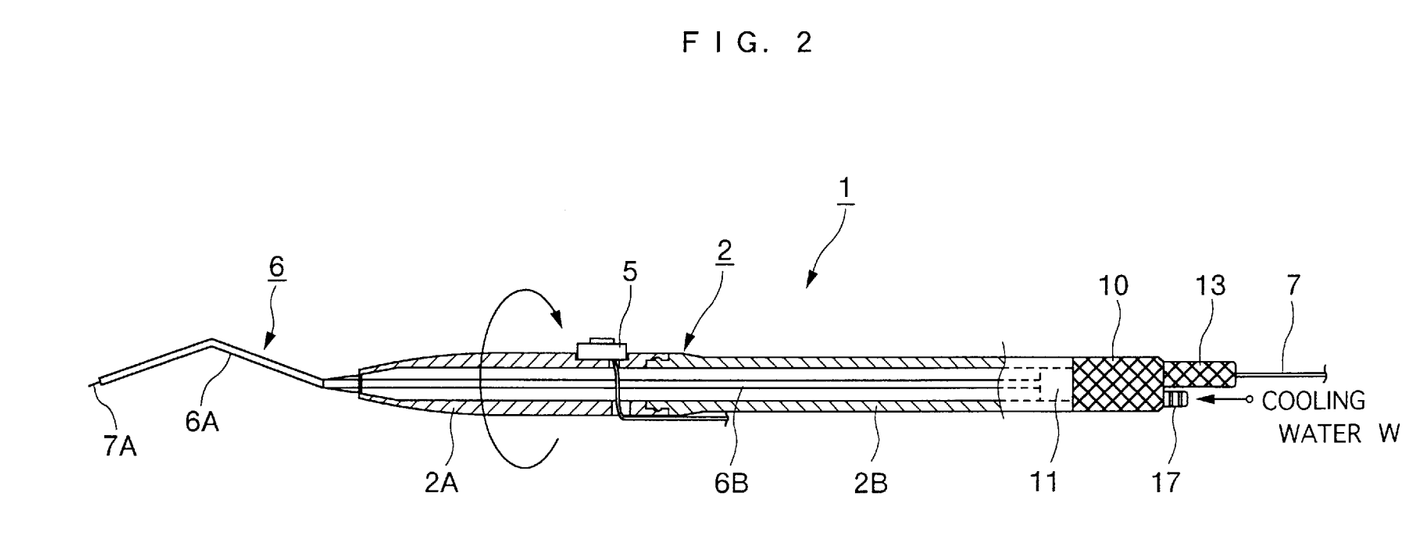
FIG. 2 is a longitudinal sectional view showing the handpiece of FIG. 1.
Figure 3:
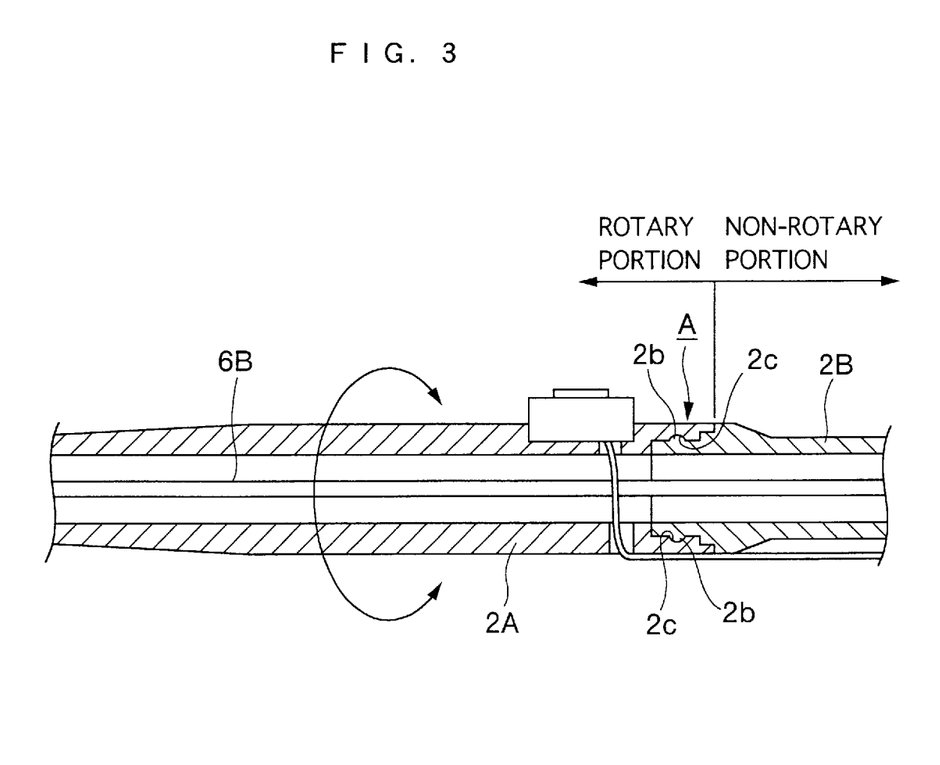
FIG. 3 is an enlarged longitudinal sectional view showing a switch portion.

The handpiece 1 mainly comprises a hand grip 2, a switch 5 on the hand grip portion 2 for controlling the laser light irradiation and a bent tube 6A for optical fibers, which is projected from the distal end of the hand grip portion 2.

The hand grip 2 comprises a rotatable cylindrical portion 2A which is on the side of the distal end and a non-rotatable cylindrical portion 2B. The rotatable cylindrical portion 2A is provided with a switch 5 for controlling the turning on or off of the laser irradiation. A lead conductor 8 from the switch 5 is connected to a laser oscillator (not shown). The non-rotatable cylindrical portion 2B is knurled on the outer surface thereof for preventing slippage so that it becomes a portion to be held by an operator. A joint portion A between the rotatable cylindrical portion 2A and the non-rotatable cylindrical portion 2B comprises a female end portion of the rotatable cylindrical portion 2A and a male end portion of the non-rotatable cylindrical portion 2B which are fitted to each other. An annular projection 2b on the outer peripheral surface of the male portion of the non-rotatable cylindrical portion 2B is engaged with an annular recess 2C (see FIG. 3) on the inner peripheral surface of the rotatable cylindrical portion 2A so that the rotatable and non-rotatable cylindrical portions 2A and 2B are not separated. Accordingly, the rotatable cylindrical portion 2A is rotatable relative to the non-rotatable cylindrical portion 2B around the longitudinal axis of the handpiece 1.

An optical fiber guide tube 6 is provided with the hand grip 2. The optical fiber guide tube 6 comprises a bent guide tube 6A which projects beyond the distal end of the hand grip 2 and is bent at an obtuse angle and a shaft tube 6B which is disposed within and substantially centrally of the hand grip 2. The optical fiber guide tube 6 is fixedly linked to handpiece connector 11. The optical fiber 7 which serves to guide laser light from the laser oscillator (not shown) is introduced into the inside of the handpiece 1 from the proximal end face of the hand grip 2 and leads to the distal end of the fiber optic guide tube 6A via the shaft tube 6B. Cooling water W is introduced to the inside of the hand grip 2 from its proximal end face and is caused to flow through a passage within the shaft tube 6B and reaches open distal end of the guide tube 6A.

Figure 4:
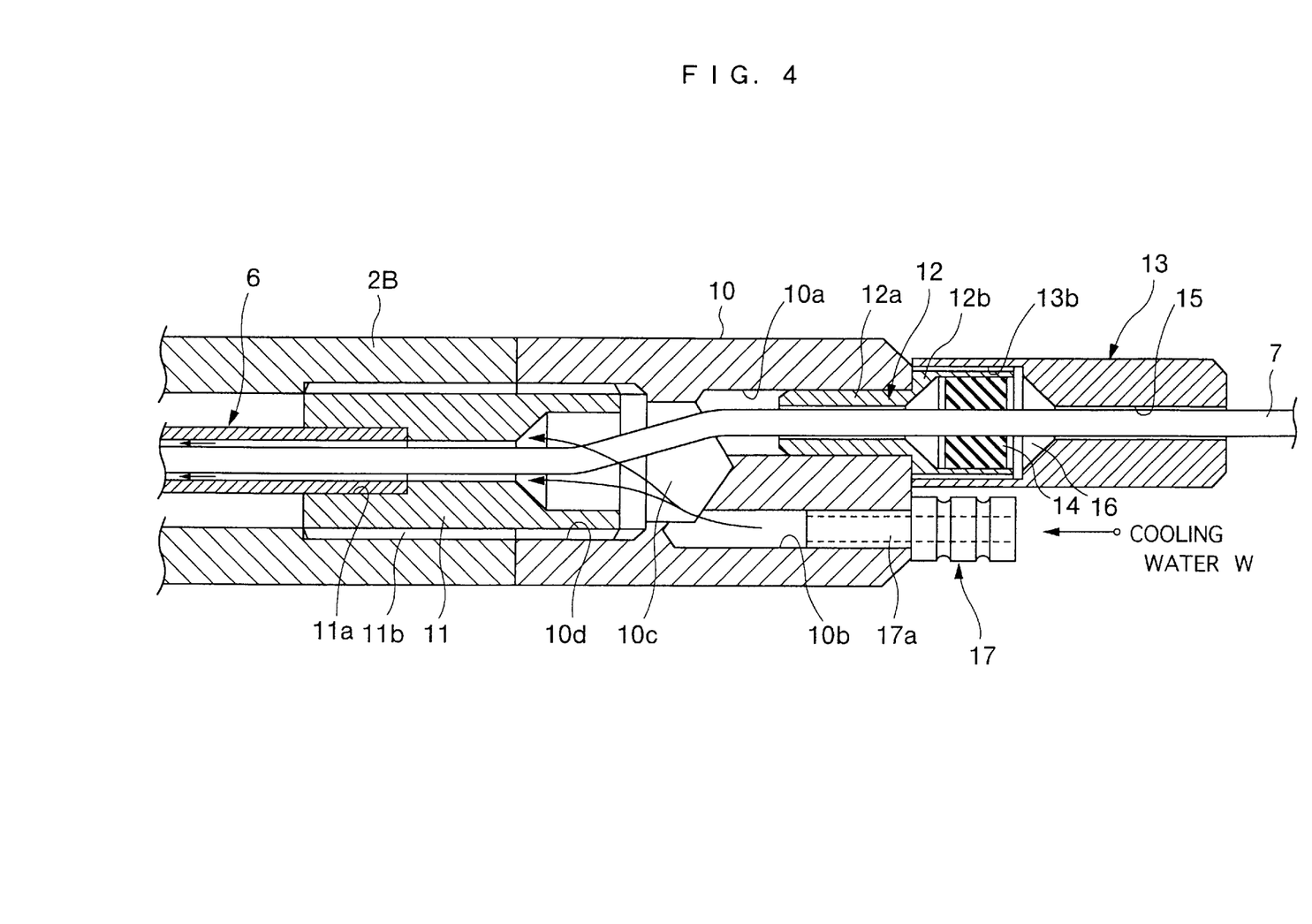
FIG. 4 is an enlarged longitudinal sectional view showing the rear portion of the hand grip.

In more detail, and with particular reference to FIG. 4 the hand grip 2 is provided at its rear end with a head piece 10. The head piece 10 is formed with a merged space 10c between an optical fiber insertion hole 10a and an inlet hole 10b of the cooling water W, and with a handpiece connector connecting internally threaded portion 10d which is contiguous the space 10c. The head piece 10 is linked with the handpiece 2 by screwing a nipple-shaped handpiece connector 11 into the connector, thereby connecting internally threaded portion 10d of the head piece 10.

On the other hand, a sleeve screw 12 and cap screw 13 are threadably engaged with the optical fiber insertion hole 10a. Specifically, a small diameter portion 12a of the sleeve screw 12 is inserted into the optical fiber insertion hole 10a and the cap screw 13 is threadably engaged with an exposed large diameter portion 12b. An optical fiber insertion hole 15 is formed through said sleeve screw 12 and the cap screw 13. In order to prevent the cooling water from returning in a reverse direction, an elastic seal member 14 is provided in an intermediate enlarged diameter space 16. The elastic seal member 14 is tightly fitted around the outer periphery of the optical fiber 7 and is in contact with the inner wall of the enlarged diameter space 16.

The optical fiber 7 is passed through the optical fiber insertion hole 15, merged space 10c and optical fiber guide tube 6, and is introduced to the distal end position of the bent guide tube 6 projecting from the hand grip 2. The distal end portion 7A of the optical fiber 7 is projected by several millimeters from the distal end of the bent guide tube 6A as shown in the drawing. Although the bent guide tube 6B is formed of a pipe member made of stainless steel in the present embodiment, it may be in an other form and made of an other material.

A connector 17 for the cooling water tube is connected to the cooling water inlet hole 10b. Connection is carried out by inserting the small diameter portion 17a of the connector 17 for the cooling water tube into the inlet tube 10b. The cooling water W which is fed via another passage flows into the optical fiber guide tube 6 via the merged space 10c and is introduced to the distal end of the bent guide tube 6A after flowing through a space within optical fiber guide tube 6 and injected forward.

Figure 5:
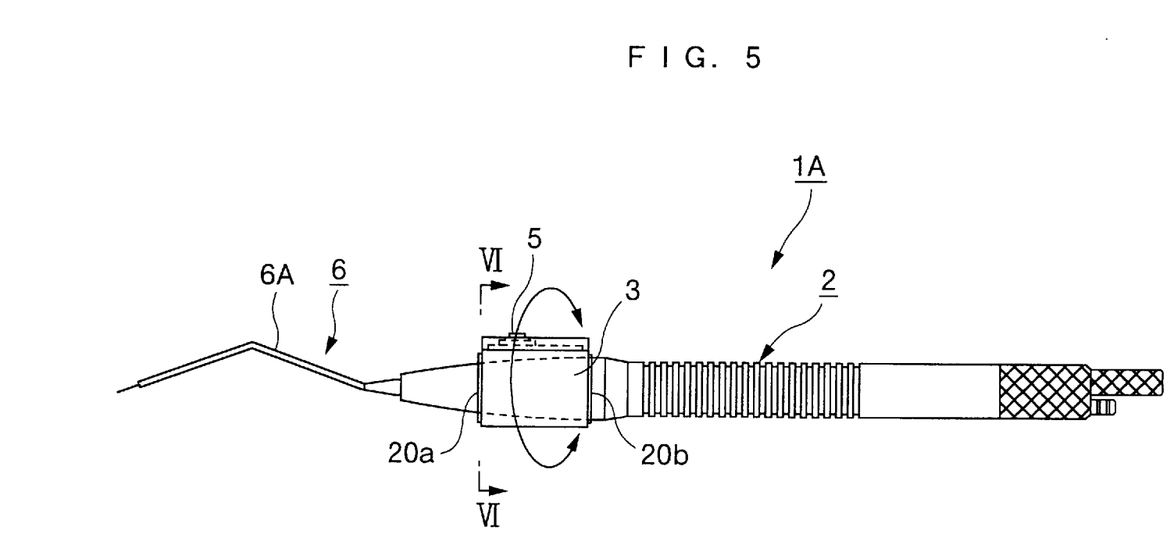
FIG. 5 is a view showing a handpiece 1A of a second embodiment of the present invention.
Figure 6:
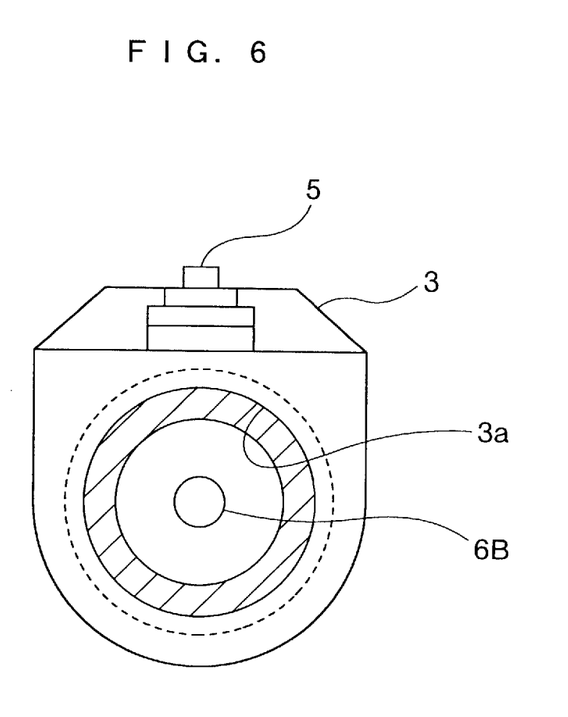
FIG. 6 is a sectional view taken along the line VI—VI in FIG. 5.

A second embodiment of a handpiece of the present invention is illustrated in FIGS. 5 and 6. In order to enable the switch 5 which is mounted on the hand grip 2 to rotate around the longitudinal axis, the handpiece 1A of the second embodiment is provided with a switch holder 3 which is fitted on the outer periphery of the hand grip 2 and the switch 5 is provided on the switch holder 3. Specifically, the switch holder 3 is formed with a through-hole 3a corresponding to the outer diameter of the hand grip 2, as shown in FIG. 6 so that the switch holder 3, is rotatably fitted on the outer periphery of the hand grip 2. Fixing rings 20a, 20b which are fixed relative to the hand grip 2 are provided in the front and rear of the hand grip 2 to prevent the switch holder 3 from forward and rearward motion after the fitting thereof. In this case, the structure of the switch can be changed without changing the structure of the hand grip 2.

A third embodiment of the handpiece is illustrated in FIGS. 7 to 10.

Figure 7:
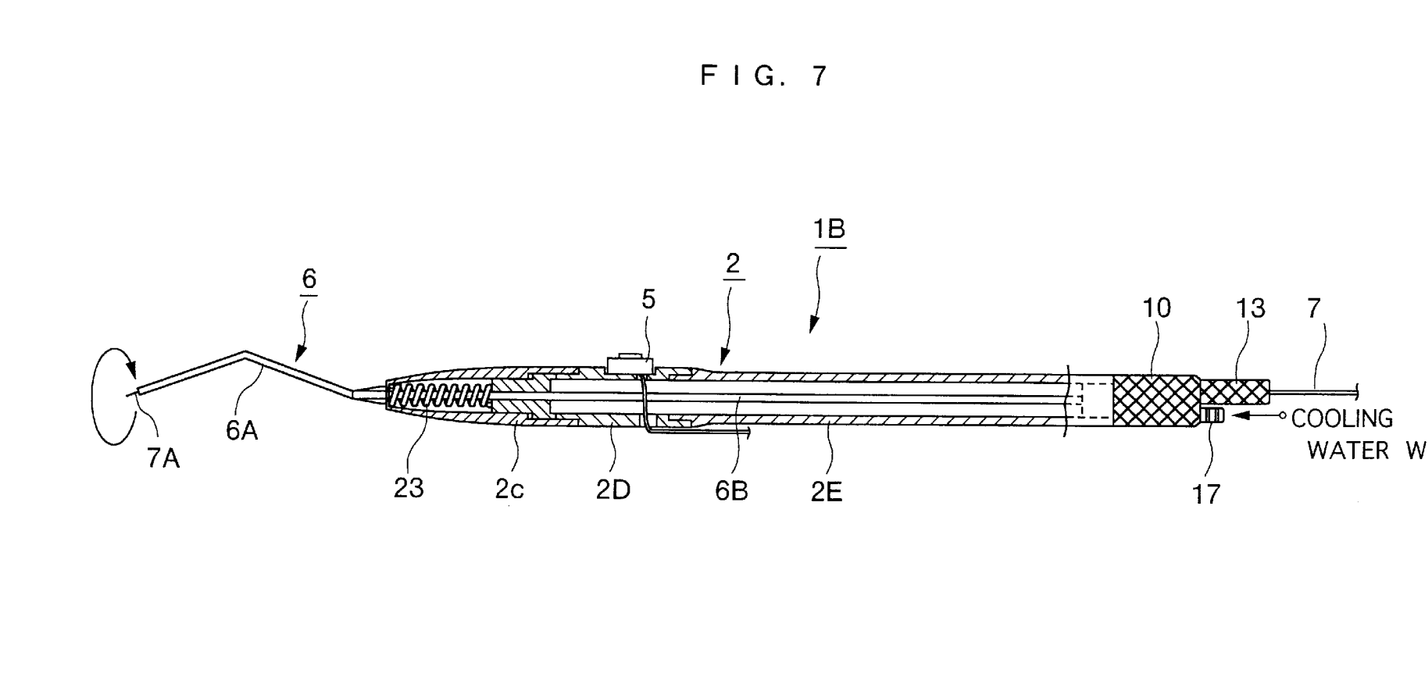
FIG. 7 is a view showing a handpiece 1B of a third embodiment of the present invention.
Figure 8:
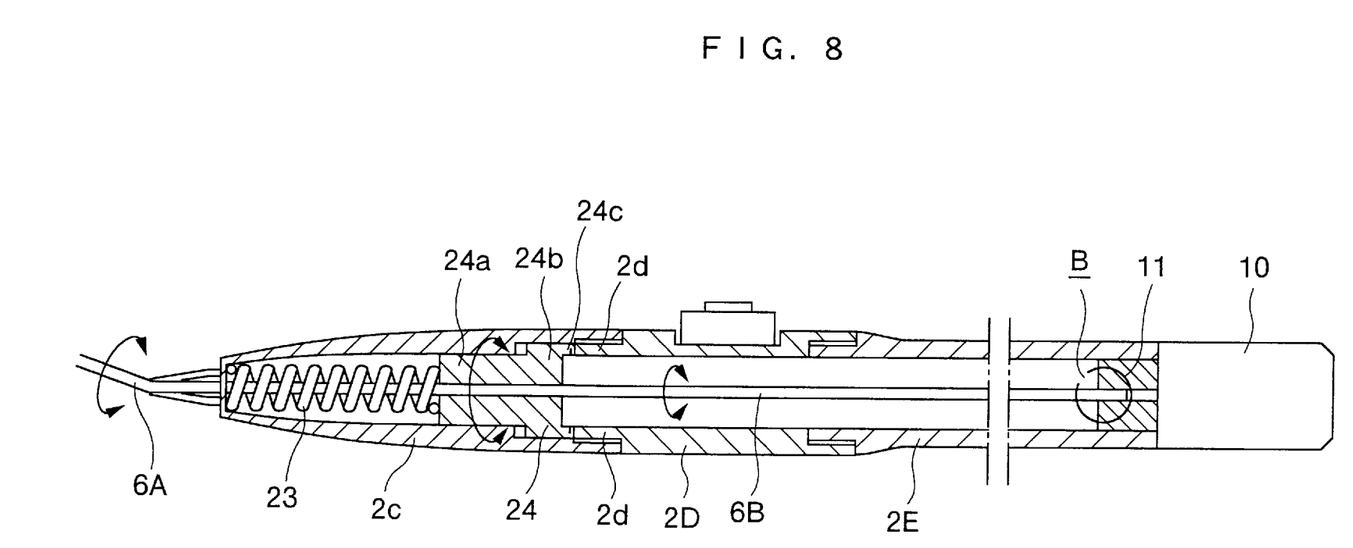
FIG. 8 is an enlarged longitudinal view showing the essential part of the handpiece 1B.

In the handpiece 1B of the third embodiment, the fiber guide tube 6 is rotatable around the longitudinal axis of the hand grip 2. In the illustrated case, the hand grip 2 comprises front, intermediate, and rear cylindrical portions 2c, 2D, and 2E, respectively. These cylindrical portions are fixedly jointed to each other by fitting the convex portion into the concave portion of respective joint portions thereof. The switch 5 is disposed on the intermediate cylindrical portion 2D.

Figure 9:
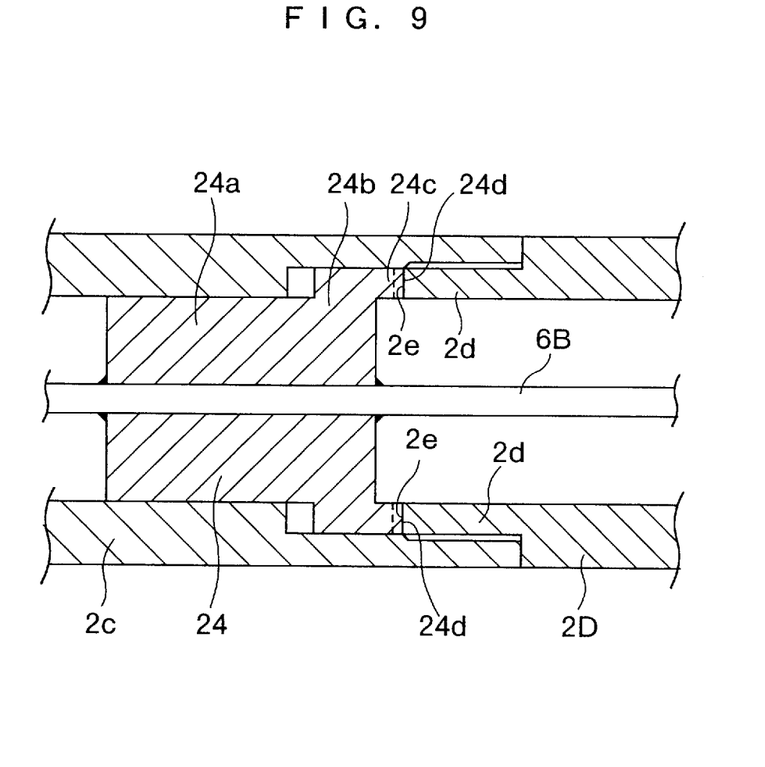
FIG. 9 is an enlarged longitudinal sectional view showing a portion where a rotational position restricting member 24 is disposed.
Figure 10:
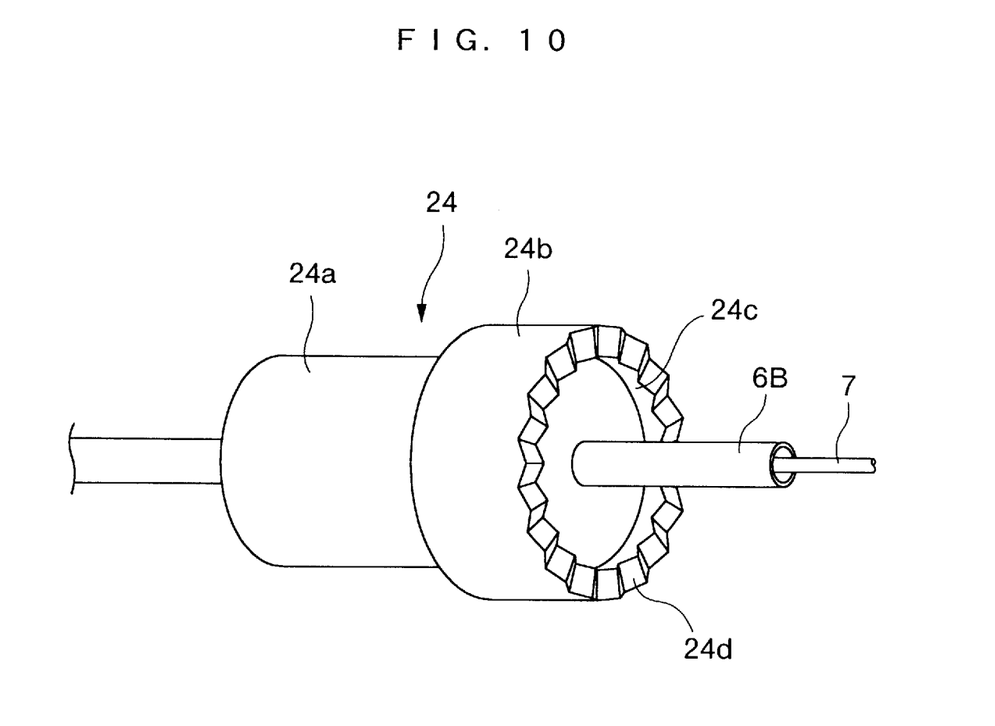
FIG. 10 is a schematic view showing the rotational position restricting member 24.

On the other hand, the shaft tube 6B of the fiber guide tube 6 is integrally provided with a member 24 for restricting the rotational position of the shaft tube 6B. The rotational position restricting member 24 comprises small and large diameter portions 24a and 24b which are on the sides of front and rear ends, respectively, as shown in FIGS. 9 and 10 in detail. The large diameter portion 24b is formed at the end face thereof with an annular projection 24c along the outer peripheral edge thereof. The annular projection is formed with serrations 24d. A fitting projection 2d of the intermediate cylindrical portion 2D is formed on its end face with serrations 2e. When the rotational position restricting member 24 is provided within the front cylindrical portion 2c, the annular projection 24c abuts the end face of the projection 2d of the intermediate cylindrical portion 2D so that opposing serrations 24d, 2e are engaged with each other. A biasing spring 23 through which the shaft tube 6B is inserted is disposed between the rotational position restricting member 24 and the distal end of the hand grip 2, so that the rotational position restricting member 24 is biased against the end face of the projection 2d of the intermediate cylindrical portion 2D.

In a joint B between the fiber guide tube 6 and the handpiece connector 11, they are not integral with each other. Accordingly, the fiber guide tube 6 will not restrict the longitudinal sliding movement and rotational movement of the member 24 around the longitudinal axis of the handpiece 1B.

Accordingly, when an operator rotates the bent guide tube 6A of the fiber guide tube 6 while tweezing it with fingers, the rotational position restricting member 24 is rotated with the fiber guide tube 6. Since the annular projection 24c of the rotational position restricting member 24 abuts the end face of the adapting projection 2d of the intermediate cylindrical portion 2D by a spring force and the serrations 24d and 2e are engaged with each other, the fiber guide tube 6 is held at each pitch of the serrations. If the fiber guide tube 6 is rotated to a predetermined position, a surgical operation is conducted while holding the handpiece 2 by depressing the switch 5 with a finger under this condition.

Since the laser irradiation switch is rotatable around the longitudinal axes of the hand grip in the dental handpiece of the present invention as mentioned above in detail, the switch can be easily actuated while irradiating the treating position with laser light for treating, particularly the upper jaw portion, the side in the oral cavity and the side of the tooth bud without the operator bending his arm or twisting his wrist.

What is claimed is:

1. A dental handpiece having a laser irradiation switch on a hand grip portion and a bent guide tube through which an optical fiber for introducing laser light to its distal end is inserted, characterized in that said laser irradiation switch can be rotated around the longitudinal axis of the handpiece together with a holder member which is fitted on the outer periphery of the hand grip and a part of the hand grip holder.

2. A dental handpiece as defined in claim 1 in which said bent guide tube further comprises a passage for supplying cooling liquid to the distal end of the guide tube.

3. A dental handpiece having a laser irradiation switch on a hand grip portion and a bent guide tube through which an optical fiber for introducing laser light to its distal end is inserted, characterized in that said bent guide tube can be rotated around the longitudinal axis of the hand grip, said bent guide tube provided with a rotational position restricting member, said restricting member having proximal and distal end faces in relation to said hand grip portion, said proximal end face formed with serrations, an end face of said hand grip portion abutting said serrated proximal end face and formed with serrations engaging therewith, and a biasing spring for resiliently urging said engaging serrations into rotationally restricted contact, whereby upon rotation of the bent guide tube by an operator, the guide tube is held at a rotational position corresponding to each pitch of the serrations.

* * * * *